United States Patent
Österle et al.

(10) Patent No.: US 6,699,250 B1
(45) Date of Patent: Mar. 2, 2004

(54) OSTEOSYNTHESIS SCREW

(75) Inventors: Helmut Österle, Feldkirch (AT); Guido Hasler, Marbach (CH); Walter Spirig, Platz-Walzenhausen (CH)

(73) Assignee: Sepitec Foundation, Vaduz (LI)

( * ) Notice: Subject to any disclaimer, the term of this patent is extended or adjusted under 35 U.S.C. 154(b) by 0 days.

(21) Appl. No.: 09/743,581
(22) PCT Filed: Jul. 9, 1999
(86) PCT No.: PCT/EP99/04845
§ 371 (c)(1), (2), (4) Date: Mar. 20, 2001
(87) PCT Pub. No.: WO00/03648
PCT Pub. Date: Jan. 27, 2000

(30) Foreign Application Priority Data
Jul. 13, 1998 (DE) .......................... 198 31 338

(51) Int. Cl.⁷ .............................. A61B 17/84
(52) U.S. Cl. ........................................ 606/73
(58) Field of Search ............... 606/62, 65, 66, 606/67, 72, 73; 411/416

(56) References Cited

U.S. PATENT DOCUMENTS

| | | | | |
|---|---|---|---|---|
| 3,681,963 A | * | 8/1972 | Muenchinger ................. 72/88 |
| 3,918,345 A | * | 11/1975 | Phipard, Jr. .................... 85/46 |
| 4,040,328 A | * | 8/1977 | Muenchinger ................. 85/46 |
| 4,046,051 A | * | 9/1977 | Lovisek ........................ 85/47 |
| 4,484,570 A | | 11/1984 | Sutter et al. |
| 5,019,079 A | | 5/1991 | Ross |
| 5,026,374 A | * | 6/1991 | Dezza et al. .................. 606/72 |
| 5,129,901 A | | 7/1992 | Decoste |
| 5,536,127 A | | 7/1996 | Pennig |
| 5,772,374 A | * | 6/1998 | Ide et al. ..................... 411/386 |

FOREIGN PATENT DOCUMENTS

| EP | 0090453 | 10/1983 | |
|---|---|---|---|
| GB | 2040769 | * 9/1980 | ............. 411/416 T |

* cited by examiner

Primary Examiner—Kevin Shaver
Assistant Examiner—Michael B. Priddy
(74) Attorney, Agent, or Firm—Volpe and Koenig, P.C.

(57) ABSTRACT

The invention relates to an osteosynthesis screw (1) comprising a shaft (3) with a thread (2) and a head (4) formed at one end and having a notch (5) for a tool. The shaft region (3) with the thread has a configuration with a uniform thickness, ie. trilobular. This configuration prevents inverse rotation due to rapid further growth of tissue

4 Claims, 1 Drawing Sheet

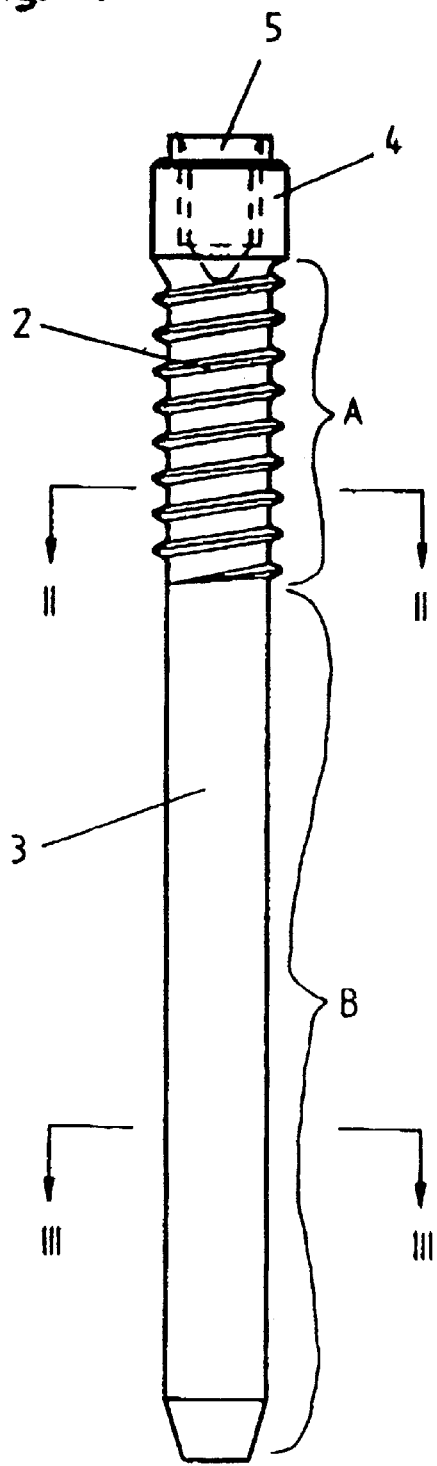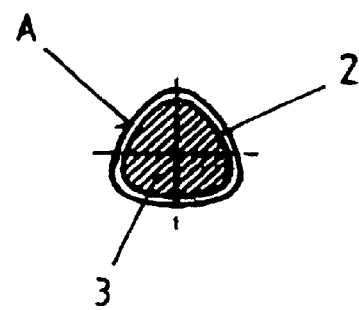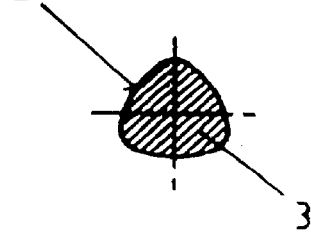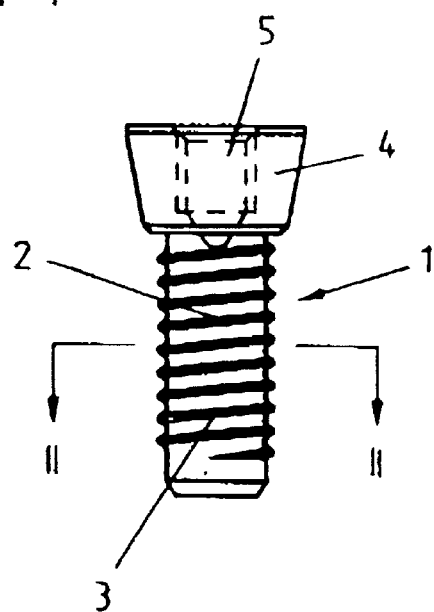

OSTEOSYNTHESIS SCREW

The invention relates to an osteosynthesis screw having a shaft, provided at least partially with a thread, as well as a tool engagement area provided at least at one end.

Osteosynthesis screws of this kind are known in various embodiments. In this connection, it was attempted to provide an improvement by a special embodiment of the head of the screw, a penetration tip at the end facing away from the head, or by a special configuration of the threaded area. It has also already been attempted to provide a reverse-lock safety for the screws which, however, has been possible only partially in combination with osteosynthesis plates to be fastened and with special additional design expenditure. A rotary locking safety is provided, of course, also in the case of bone marrow nails which are provided with longitudinal ribs or grooves. In the case of such bone marrow nails there is however no possibility for an axial securing action. In the case of locking nails there is the possibility of axial securing.

From U.S. pat. No. 5,026,374 an orthopedic-surgical screw is known which is used in a device, for example, a mono-axial extension device, for external fixation. This known screw has a thread-free central portion which in cross-section is drop-shaped and is provided with an axially extending cutting edge. This central portion does not come into contact with the bone but only with the soft tissue external to the bone. Moreover, the known screw has a cylindrical end portion provided with an outer thread which is provided for screwing into bone material. When this end portion is screwed into a bone, the screw is not secured against rotation.

The present invention has therefore the object to provide an osteosynthesis screw of the aforementioned kind with which in a simple way a rotary locking action as well as a safety against self-acting axial displacement is possible.

According to the invention this is achieved in that the area of the shaft with the thread and/or a thread-free area of the shaft engaging the bone is noncircular, in the manner of an orbiform curve, for example, trilobular or polygonal.

With this feature according to the invention it is achieved that the osteosynthesis screw can be screwed in like a screw, wherein the area of the shaft with the thread by means of thread engagement provides an axial securing action against a self-acting displacement. With the embodiment of the area with the thread and/or a possibly present thread-free area according to the present invention, an optimal rotary locking action is provided also. However, the tight seat of a screw in the drilled hole occurring in metal construction is not employed in this connection because especially in the area of a bone these radial forces cannot act on the screw. By means of the noncircular, or the like, cross-sectional shape of the threaded area or of a thread-free area, a positive-locking connection between the bone material and the displacement in the axial direction as a result of the presence of a thread.

In spite of this, a later loosening of such a screw is possible in a simple manner. The ingrowing bone will yield already upon application of a small torque onto the osteosynthesis screw so that it can be unscrewed without problems if this is necessary. As a result of the noncircular configuration it is only achieved that the osteosynthesis screw cannot self-actingly become loose and then unscrew itself. Accordingly, only minimal forces are required for the position securing action against rotation and against axial displacement.

In order to be able to screw the osteosynthesis screw in a conventional manner easily into a pre-drilled hole, it is provided that the thread on the shaft is self-tapping and/or self-cutting. The osteosynthesis screw acts thus always in a self-shaping way with respect to producing the thread in the drilled hole.

One embodiment provides that the thread and the shaft in this area are cylindrically designed, wherein the thread-free area of the shaft adjoining the area of the shaft with the thread at one or both ends is noncircular, in the fashion of an orbiform curve, for example, trilobular or polygonal, and/or is provided with projections and/or depressions. Accordingly, an osteosynthesis screw can be used in which a conventional thread is employed, wherein then however a thread-free area engaging the bone area is noncircular or the like. In such a case the thread provides the securing action against an axial displacement of the osteosynthesis screw and the thread-free area of the shaft, which is noncircular or the like, effects the rotary locking action by positive-locking engagement with the ingrowing bone. action against rotation and against axial displacement.

In order to be able to screw the osteosynthesis screw in a conventional manner easily into a pre-drilled hole, it is provided that the thread on the shaft is self-tapping and/or self-cutting. The osteosynthesis screw acts thus always in a self-shaping way with respect to producing the thread in the drilled hole.

Embodiments of the invention will be explained in more detail in the following description with the aid of the drawing. It is shown in:

FIG. 1 an osteosynthesis screw in a side view;

FIG. 2 a section along the line II—II of FIG. 1 or along the line II—II of FIG. 4;

FIG. 3 a section along the line III—III of FIG. 4;

FIG. 4 a second embodiment of the osteosynthesis screw according to the invention.

In an osteosynthesis screw 1 having a shaft 3 with a thread 2 as well as a head 4 formed at least at one end and provided with a tool engagement area 5, the shaft 3 and thus also the thread 2 are embodied with a trilobular shape. Such trilobular threads 2 (see also the section according to FIG. 2) are used in mechanical engineering technology for producing a thread in a drilled hole. In connection with osteosynthesis screws such embodiments are not used because a person skilled in the art is aware that the manufacture of a thread in such a pre-drilled hole in a bone presents no problems as a result of the consistency of the bone material. In this connection, this trilobular thread is also not primarily required in order to indeed produce the thread but in order to effect a rotary locking action of the osteosynthesis screw because the quickly ingrowing tissue will immediately surround this noncircular cross-section of the osteosynthesis screw in a positive-locking manner, and over time also the slowly ingrowing bone material. The most common form for the embodiment of a thread of this type is a cross-section according to an orbiform, and in this connection, in particular, a trilobular shape.

In the context of the invention any kind of a noncircular embodiment of the threaded area or of the thread-free area, a polygonal embodiment or also any other shape according to the configuration of an orbiform is possible, wherein also, instead of these cross-sectional shapes, or in addition thereto, projections and/or depressions can be provided. In this connection it is of no consequence for which application in the medical technology these screws are to be used. The embodiment according to the invention can be used in connection with osteosynthesis screws or metal, for example, stainless steel, titanium, CoCr alloys or suitable noble metals, as well as polymers, optionally reinforced with glass fibers, or ceramics. The thread 2 on the osteosynthesis screw 1 can be a self-cutting and/or self-tapping thread, i.e., a thread designed one way or another to self-generate a thread.

In the embodiment according to FIG. 4, an osteosynthesis screw is provided which has an area A with a thread 2 and a thread-free area B. Such osteosynthesis screws are required for special applications wherein only a relatively short area A with a thread 2 is required in order to effect the axial securing action of the screw. The entire length of the shaft 3 is only required in order to secure the bones in the desired aligned position. In this connection, only the area A with the thread 2 and/or the thread-free area B of the shaft 3 (see also illustration of FIG. 3) can be embodied to be noncircular or the like. It is only necessary to ensure the rotary locking action in cooperation with the ingrowing bone by means of a special embodiment of an area A and/or B of the shaft 3. Accordingly, it is also conceivable that the thread 2 and the shaft 3 in this area A are of a cylindrical embodiment. The thread-free area B of the shaft 3 adjoining at one or both ends the area A with the thread 2 is then noncircular, in the form of an orbiform curve, for example, trilobular or polygonal, and/or is provided with projections and/or depressions. Accordingly, it is thus possible to employ an osteosynthesis screw which is provided with a conventional thread wherein then however the thread-free area engaging the bone area is noncircular or the like. In such a case, the thread provides the securing action against an axial displacement of the osteosynthesis screw and the thread-free area of the shaft, which in cross-section is noncircular or the like, effects by positive-locking connection with the ingrowing bone the rotary locking action.

In the context of the invention it would also be possible to provide a partial section or the entire length of the thread-free area B of the shaft 3 with radially surrounding grooves and/or ribs. These grooves and/or ribs can additionally contribute to the rotary locking action and to the axial securing action. The area A with the thread 2 can also be formed in a central area or with smaller spacing from the head 5 of the osteosynthesis screw so that then at both ends of the area A with the thread 2 areas B without thread are provided. It is then also possible to embody only one such thread-free area B with a noncircular design or the like. It would also be conceivable to configure the osteosynthesis screw 1 for special applications in a self-drilling form, i.e., with a free end provided in the form of a penetration tip or with a corresponding drill part.

Moreover, it would be possible to provide, in addition to the areas A or B of the shaft or instead of these areas, the area of the head of an osteosynthesis screw with a noncircular design or to provide it with projections and/or depressions. Such a configuration is especially expedient and advantageous in connection with osteosynthesis plates or with a counter sunk arrangement of the head of the osteosynthesis screw.

What is claimed is:

1. An osteosynthesis screw for engaging a bone and having a shaft, which is at least partially provided with a thread, as well as a tool engaging area provided at least at one end, characterized in that at least one of an area (A) of the shaft (3) with the thread (2) and a thread-free area (B) of the shaft (3) is noncircular, in the shape of an orbiform curve, whereby elastic adaptation and ingrowing of the bone prevent inverse screwing and axial displacement of the screw, and in that the thread-free area (3) is substantially longer than the area (A) with the thread.

2. An osteosynthesis screw according to claim 1, characterized in that the thread (2) is formed on the shaft (3) as a self-tapping and/or self-cutting thread.

3. The osteosynthesis screw of claim 1, wherein the orbiform is trilobular or polygonal.

4. The osteosynthesis screw of claim 1 wherein the area (A) with the thread is orbiform.

* * * * *